(12) United States Patent
Numata et al.

(10) Patent No.: US 12,185,920 B2
(45) Date of Patent: Jan. 7, 2025

(54) GAS FEEDING APPARATUS, SUPPLY METHOD AND GAS FEEDING SYSTEM FOR STOPPING AND REDUCING GAS FEEDING BASED ON SET THRESHOLD

(71) Applicant: OLYMPUS CORPORATION, Tokyo (JP)

(72) Inventors: Goki Numata, Hachioji (JP); Kunitoshi Hiraga, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 680 days.

(21) Appl. No.: 17/476,847

(22) Filed: Sep. 16, 2021

(65) Prior Publication Data

US 2022/0000349 A1  Jan. 6, 2022

Related U.S. Application Data

(63) Continuation of application No. PCT/JP2019/011792, filed on Mar. 20, 2019.

(51) Int. Cl.
*A61B 1/015* (2006.01)
*A61B 1/00* (2006.01)

(52) U.S. Cl.
CPC .......... *A61B 1/015* (2013.01); *A61B 1/00068* (2013.01); *A61B 2562/0247* (2013.01); *A61M 2205/3334* (2013.01)

(58) Field of Classification Search
USPC .................................................. 600/158, 159
See application file for complete search history.

(56) References Cited

U.S. PATENT DOCUMENTS

2006/0030751 A1  2/2006 Uesugi et al.
2007/0244363 A1* 10/2007 Sano .................... A61M 13/003
                                                            600/118
(Continued)

FOREIGN PATENT DOCUMENTS

JP        H11-342108 A    12/1999
JP        2006-043130 A    2/2006
(Continued)

OTHER PUBLICATIONS

International Search Report dated May 21, 2019 received in PCT/JP2019/011792.

*Primary Examiner* — John P Leubecker
(74) *Attorney, Agent, or Firm* — Scully, Scott, Murphy & Presser, P.C.

(57) ABSTRACT

A gas feeding apparatus configured to supply the gas to a lumen of a patient through a gas feeding conduit provided in an endoscope, the gas feeding apparatus including: a flow rate sensor configured to measure a flow rate of the gas in the gas feeding conduit; and a control circuit configured to time-sequentially calculate an integrated amount of the gas fed to the lumen in a period from a first timing to a second timing, the first timing being a timing when the gas starts to be fed from the gas feeding conduit to the lumen by an operation of a gas feeding button of the endoscope, the second timing being different from the first timing. The control circuit controls a notification unit to activate an alarm, when the integrated amount of the gas reaches the first threshold.

16 Claims, 6 Drawing Sheets

(56) References Cited

U.S. PATENT DOCUMENTS

| | | | | |
|---|---|---|---|---|
| 2010/0228100 A1* | 9/2010 | Vining | ............... | A61B 5/03 600/300 |
| 2012/0130304 A1* | 5/2012 | Barish | ............ | A61M 13/003 604/24 |
| 2014/0066839 A1* | 3/2014 | Torisawa | .......... | A61M 13/003 604/26 |
| 2019/0274532 A1* | 9/2019 | Buch | ................ | A61B 1/3132 |

FOREIGN PATENT DOCUMENTS

| | | |
|---|---|---|
| JP | 2006-288881 A | 10/2006 |
| JP | 2014-140535 A | 8/2014 |

* cited by examiner

GAS FEEDING APPARATUS, SUPPLY METHOD AND GAS FEEDING SYSTEM FOR STOPPING AND REDUCING GAS FEEDING BASED ON SET THRESHOLD

CROSS REFERENCE TO RELATED APPLICATION

This application is a continuation application of PCT/JP2019/011792 filed on Mar. 20, 2019, the entire contents of which are incorporated herein by this reference.

BACKGROUND OF THE INVENTION

1. Field of the Invention

An embodiment of the present invention relates to a gas feeding apparatus, particularly, a gas feeding apparatus that is connected with an endoscope apparatus and that injects air or an inactive gas from a distal end of the endoscope apparatus into an abdominal cavity or a lumen, and relates to a supply method and a gas feeding system.

2. Description of the Related Art

In recent years, an endoscope has been widely used. The endoscope is used for observing organs and the like in a lumen of a patient and performing various curative treatments to sites and tissues in the lumen using treatment instruments as necessary. For the observation and various treatments using the endoscope, a gas feeding apparatus is used for purpose of securing a viewing field of the endoscope and purpose of securing a region for operating treatment instruments.

The gas feeding apparatus injects carbon dioxide gas or the like to an operative field in a body cavity, as a gas for a gas feeding, and secures the viewing field of the endoscope and the operation region for treatment instruments (see Japanese Patent Application Laid-Open Publication No. 2006-43130, for example). Generally, an insufflation apparatus that feeds the gas into the body cavity of the patient and that expands the body cavity includes pressure monitoring means, and is configured to be capable of automatically feeding the gas depending on a pressure setting value. In contrast, the gas feeding apparatus has no pressure monitoring means, and an operator or the like instinctively determines a gas feeding amount, and manually controls timings of start and stop of the gas feeding.

SUMMARY OF THE INVENTION

A gas feeding apparatus in an aspect of the present invention is a gas feeding apparatus communicating with a gas feeding source that feeds a predetermined gas, the gas feeding apparatus being configured to supply the gas to a lumen of a patient through a gas feeding conduit provided in an endoscope, the gas feeding apparatus including a control circuit, the control circuit being configured to: measure a flow rate of the gas in the gas feeding conduit, based on an output of a flow rate measurement device; time-sequentially calculate an integrated amount of the gas fed to the lumen in a period from a first timing to a second timing, the first timing being a timing when the gas starts to be fed from the gas feeding conduit to the lumen by an operation of a gas feeding button of the endoscope, the second timing being different from the first timing; set a first threshold for the integrated amount of the gas; and control a notification device to activate an alarm, when the integrated amount of the gas reaches the first threshold in the period from the first timing to the second timing.

A supply method according to an aspect of the present invention is a supply method for supplying a predetermined gas to a lumen of a patient through a gas feeding conduit provided in an endoscope, the supply method including: measuring a flow rate of the gas in the gas feeding conduit; time-sequentially calculating an integrated amount of the gas fed to the lumen in a period from a first timing to a second timing, the first timing being a timing when the gas starts to be fed from the gas feeding conduit to the lumen by an operation of a gas feeding button of the endoscope, the second timing being different from the first timing; and activating an alarm when the integrated amount of the gas reaches a first threshold in the period from the first timing to the second timing.

A gas feeding system according to an aspect of the present invention is a gas feeding system that includes an endoscope including a gas feeding conduit and a gas feeding apparatus communicating with a gas feeding source that feeds a predetermined gas, the gas feeding apparatus being configured to supply the gas to a lumen of a patient through the gas feeding conduit, the gas feeding apparatus including a control circuit, the control circuit being configured to: measure a flow rate of the gas in the gas feeding conduit, based on an output of a flow rate measurement device; time-sequentially calculate an integrated amount of the gas fed to the lumen in a period from a first timing to a second timing, the first timing being a timing when the gas starts to be fed from the gas feeding conduit to the lumen by an operation of a gas feeding button of the endoscope, the second timing being different from the first timing; set a first threshold for the integrated amount of the gas; and control a notification device to activate an alarm, when the integrated amount of the gas reaches the first threshold in the period from the first timing to the second timing.

DETAILED DESCRIPTION OF THE PREFERRED EMBODIMENTS

Embodiments will be described below with reference to the drawings.

First Embodiment

Figure 1:
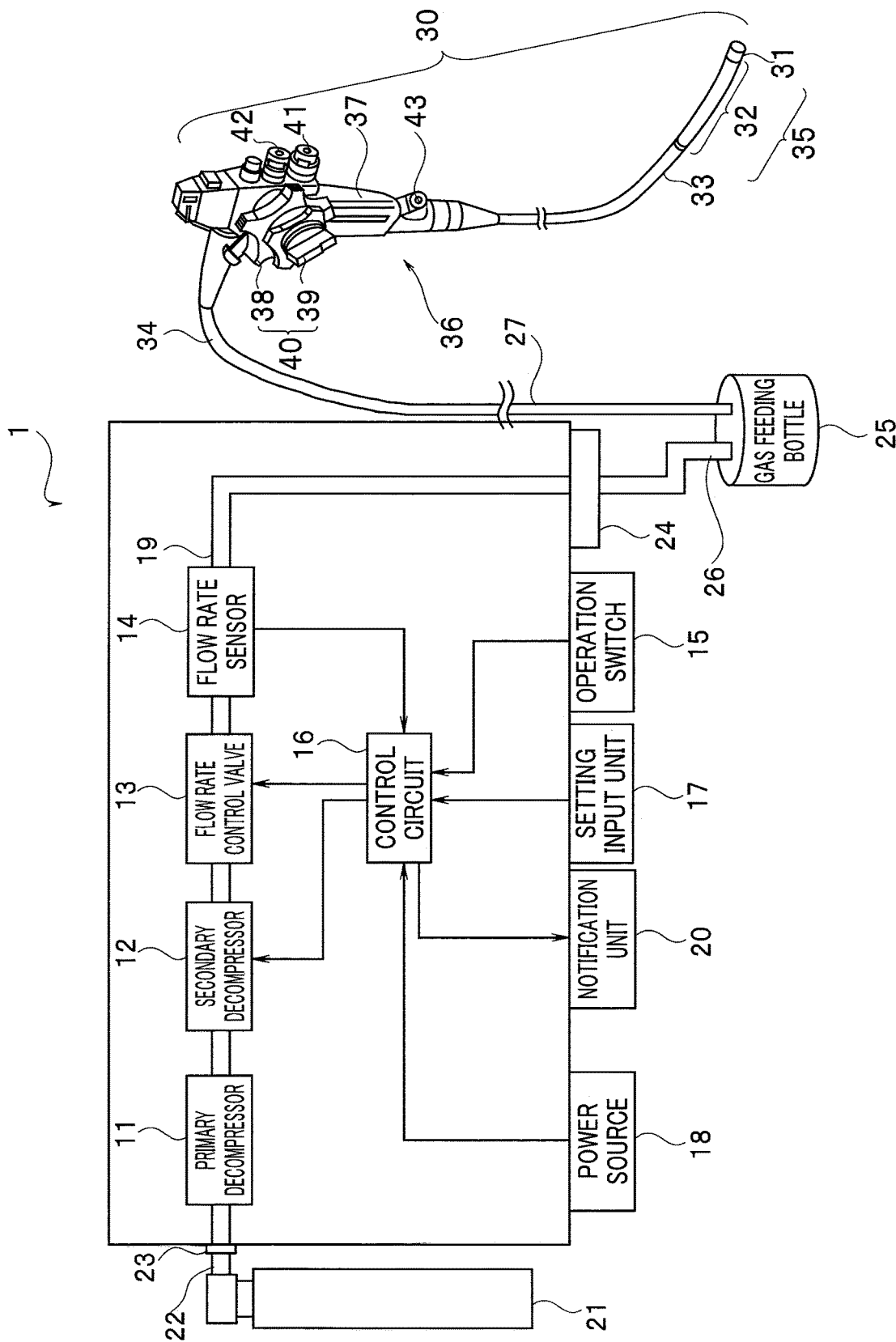
FIG. 1 is a diagram for describing an example of a whole configuration of a gas feeding system using a gas feeding apparatus 1 according to a first embodiment of the present invention.

FIG. 1 is a diagram for describing an example of a whole configuration of a gas feeding system using a gas feeding apparatus 1 according to a first embodiment of the present invention. As shown in FIG. 1, the gas feeding system in the embodiment is configured by the gas feeding apparatus 1 and a gas feeding bottle 25.

The gas feeding apparatus 1 is connected with a gas supply source 21 (for example, a carbon dioxide gas cylinder) through a high-pressure gas hose 22. The other end of the high-pressure gas hose 22 is connected with a high-pressure connector 23 provided on the gas feeding apparatus 1. Further, a gas feeding connector 24 is provided on the gas feeding apparatus 1, and one end of a gas feeding tube 26 is connected with the gas feeding connector 24. The other end of the gas feeding tube 26 is connected with a gas feeding bottle 25 as a gas reserve unit. One end of a gas feeding tube 27 is connected with the gas feeding bottle 25. The other end of the gas feeding tube 27 is connected with an unillustrated gas feeding conduit through an unillustrated endoscope connector. The gas feeding conduit is inserted in a universal cable 34 connected with an endoscope 30.

The endoscope 30 is configured to include an insertion unit 35 having a long size and an elongated shape, an operation unit 36, and the universal cable 34. The insertion unit 35 of the endoscope 30 is configured to include a distal end portion 31, a bending portion 32 and a flexible tube portion 33, in an order from a distal end. At the distal end portion 31, an objective lens (not illustrated) that forms an image of a subject is disposed. Furthermore, at an image formation position of the objective lens, a solid-state image pickup device (not illustrated) such as a CCD and a CMOS is disposed as image pickup means.

On the operation unit 36, a bending operation knob 40 for performing a bending operation of the bending portion 32 of the insertion unit 35 is arranged in a rotatable manner, and switches for various endoscope functions, and the like are provided. Note that an UD bending operation knob 38 and an RL bending operation knob 39 are arranged so as to be superimposed on each other in the bending operation knob 40. By the UD bending operation knob 38, the bending operation of the bending portion 32 is performed in an up-down direction, and by the RL bending operation knob 39, the bending operation of the bending portion 32 is performed in a right-left direction. Furthermore, a gas feeding button 41 for supplying a gas such as carbon dioxide and a liquid such as water into the lumen, and a suction button 42 are provided on the operation unit 36.

A joining portion between the insertion unit 35 and the operation unit 36 is configured to include a grasping portion 37 and a treatment instrument channel insertion portion 43. The grasping portion 37 also serves as a grasping portion for a user. The treatment instrument channel insertion portion 43 is arranged on a bend preventing portion provided between the grasping portion 37 and one end of the flexible tube portion 33 of the insertion unit 35, and serves as an opening portion of a treatment instrument channel into which various treatment portions arranged on the insertion unit 35 are inserted.

The universal cable 34 extended from the operation unit 36 includes an unillustrated endoscope connector at an extension end. The gas feeding tube 27 extended from the gas feeding bottle 25 is connected with an unillustrated gas feeding conduit inserted in the universal cable 34, through the endoscope connector. In other words, the gas discharged from the gas feeding apparatus 1 is supplied to the unillustrated gas feeding conduit, through the gas feeding tube 26, the gas feeding bottle 25 and the gas feeding tube 27. The gas supplied to the gas feeding conduit is supplied from the distal end portion 31 of the insertion unit 35 into the lumen, when a gas feeding button 41 of the operation unit 36 is pressed down.

In the gas feeding apparatus 1, a primary decompressor 11, a secondary decompressor 12, a flow rate control valve 13 and a flow rate sensor 14 as a flow rate measurement device are provided, and the sites are connected in this order, by a gas feeding conduit 19 formed of silicone, fluorine resin or the like. Further, the gas feeding apparatus 1 is provided with a control circuit 16, a setting input unit 17, an operation switch 15, a power source 18, and a notification unit 20 as a notification device.

The primary decompressor 11 and the high-pressure connector 23 are connected by the gas feeding conduit 19, and the flow rate sensor 14 and the gas feeding connector 24 are connected by the gas feeding conduit 19. In other words, the gas fed from the gas supply source 21 and supplied to the gas feeding apparatus 1 through the high-pressure gas hose 22 passes through the primary decompressor 11, the secondary decompressor 12, the flow rate control valve 13 and the flow rate sensor 14 in this order, along the gas feeding conduit 19. After adjustment to a predetermined pressure and flow rate, the gas is discharged from the gas feeding tube 26 through the gas feeding connector 24.

The primary decompressor 11 and the secondary decompressor 12 decompress the gas such as carbon dioxide, which is supplied through the high-pressure connector 23, to a pressure that is not dangerous to human bodies. For example, the primary decompressor 11 and the secondary decompressor 12 decompress the gas supplied from the gas supply source 21 at a high pressure of about several MPa to about 6 kPa to 100 kPa.

The flow rate control valve 13 is configured to be capable of adjusting the flow rate of the gas to be supplied to the endoscope 30, to a predetermined value. For example, the flow rate control valve 13 is a kind of an electromagnetic drive valve, and is configured by a control valve in which an electromagnetic coil is used as a drive unit. When electric current is caused to flow through the electromagnetic coil, magnetic force is generated, and a plunger is pulled, so that the valve is opened or closed. The flow rate control valve 13 is configured to be capable of controlling the opening degree of a valve unit and adjusting the flow rate of the gas that flows through the gas feeding conduit to a predetermined value, by controlling the position of the plunger with the magnitude of the electric current that is caused to flow through the electromagnetic coil.

The flow rate sensor 14 measures the flow rate of the gas that is supplied into the lumen, and outputs a measurement result to the control circuit 16.

The operation switch 15 is a user interface through which the user or the like inputs an instruction of gas feeding start or gas feeding stop. The instruction from the operation switch 15 is outputted to the control circuit 16.

The setting input unit 17 is a user interface through which the user or the like inputs settings of the gas feeding flow rate and various thresholds and others to trigger a flow rate control and an alarm notification. The instruction content from the setting input unit 17 is outputted to the control circuit 16.

The power source 18 switches on-off of power supply to each site of the gas feeding apparatus 1.

The control circuit 16 as a control unit time-sequentially integrates a gas feeding amount in a designated period from a time point T1 to a time point T2, based on the flow rate measurement value inputted from the flow rate sensor 14.

Figure 2:
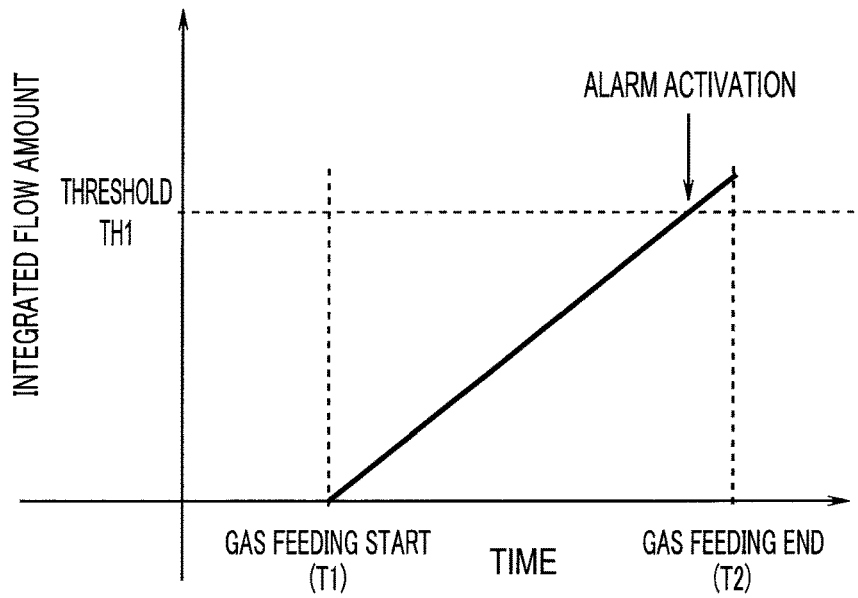
FIG. 2 is a diagram for describing an alarm activation timing based on an integrated flow amount.

FIG. 2 is a diagram for describing an alarm activation timing based on an integrated flow amount. For example, the time point T1 is a timing when the gas feeding button 41 of the endoscope 30 is pressed down and the gas starts to be fed from the distal end portion 31 of the insertion unit 35 into the lumen. While the pressed-down state of the gas feeding button 41 is continued, the gas feeding is continued. As the time point T2, it is possible to adopt a timing when the pressed-down state of the gas feeding button 41 of the endoscope 30 is released and the gas stops being fed from the distal end portion 31 of the insertion unit 35 into the lumen.

The control circuit 16 activates an alarm to the user by causing the notification unit 20 to act, at the time when the integrated gas feeding amount reaches a previously set threshold TH1, in the period from the time point T1 to the time point T2. As the action of the notification unit 20 at the time of the alarm activation, for example, the notification unit 20 causes the user to visually perceive the alarm by lighting a lamp or causes the user to aurally perceive the alarm by activating a buzzer or a warning message.

For example, the threshold TH1 can be set as follows. Here, a case where the gas feeding flow rate is relatively high and an excessive gas feeding easily occurs is discussed. For example, in the case of 1.5 L/min, among ratios of gas feeding time periods in examinations, the most frequent gas feeding time period tends to be 11 seconds to 20 seconds, and the second most frequent gas feeding time period tends to be 20 seconds or more. In other words, a gas feeding time period of 20 seconds or more can lead to the excessive gas feeding. When a temporal margin is 50%, an allowed time period is 30 seconds. The gas feeding amount for 30 seconds is $1.5\times(30/60)=0.75$ L. Accordingly, the threshold TH1 for one gas feeding can be set to 0.75 L. Generally, it is preferable that the threshold TH1 should be set to a predetermined flow amount between 0.1 L and 10 L, which is just one example because the gas feeding flow rate and the gas feeding time period vary depending on a procedure, a gas feeding site and an operator.

Note that the timing when the gas starts to be fed from the distal end portion 31 of the insertion unit 35 into the lumen can be estimated from the measurement value of the flow rate sensor 14. At the time when the gas feeding into the lumen is not performed, the value of the flow rate sensor 14 is a very small value close to zero. When the gas feeding of the gas into the lumen is started, the value of the flow rate sensor 14 rises. Accordingly, it can be estimated that the timing when the gas feeding is started is a time when the value of the flow rate sensor 14 starts to rise from a value close to zero. Similarly, the timing when the gas feeding of the gas into the lumen is stopped can be estimated from the measurement value of the flow rate sensor 14. In other words, while the gas feeding is stably performed, the flow rate sensor 14 keeps a set flow rate value Lc. When the gas feeding of the gas into the lumen is stopped, the value of the flow rate sensor 14 decreases. It can be estimated that the timing when the gas feeding is stopped is a time when the value of the flow rate sensor 14 decreases from the set flow rate value Lc.

In this way, according to the embodiment, the control circuit 16 estimates the time points T1, T2, by monitoring change in the measurement value of the flow rate sensor 14. Then, the control circuit 16 calculates the integrated gas feeding amount to the lumen, by time-sequentially integrating the measurement value of the flow rate sensor 14 in the period from the time point T1 to the time point T2. At the time when the integrated gas feeding amount reaches the previously set threshold TH1, the control circuit 16 activates the alarm by causing the notification unit 20 to act, and thereby, the user can recognize the integrated gas feeding amount. Accordingly, even when the user is concentrating on the observation or treatment of an organ in the lumen and loses awareness about the gas feeding, it is possible to raise awareness about the gas feeding at a necessary time, and to prevent the excessive gas feeding into the lumen.

Note that although the configuration of the system that can perform the gas feeding to the lumen has been described above as an example, the embodiment can be applied to a gas/water feeding system that can perform not only gas feeding but also water feeding. In the gas/water feeding system, a water feeding bottle is used as the gas feeding bottle 25, and a gas; water feeding button that allows switching and execution of the gas feeding and the water feeding is used as the gas feeding button 41.

Although the determination about the alarm is performed by integrating the flow amount in one gas feeding period from the gas feeding start to the gas feeding end as described above, the flow amount from the start of the procedure to the end of the procedure may be integrated. In other words, the timing of the procedure start may be adopted as the time point T1, and the timing of the procedure end may be adopted as the time point T2.

Figure 3:
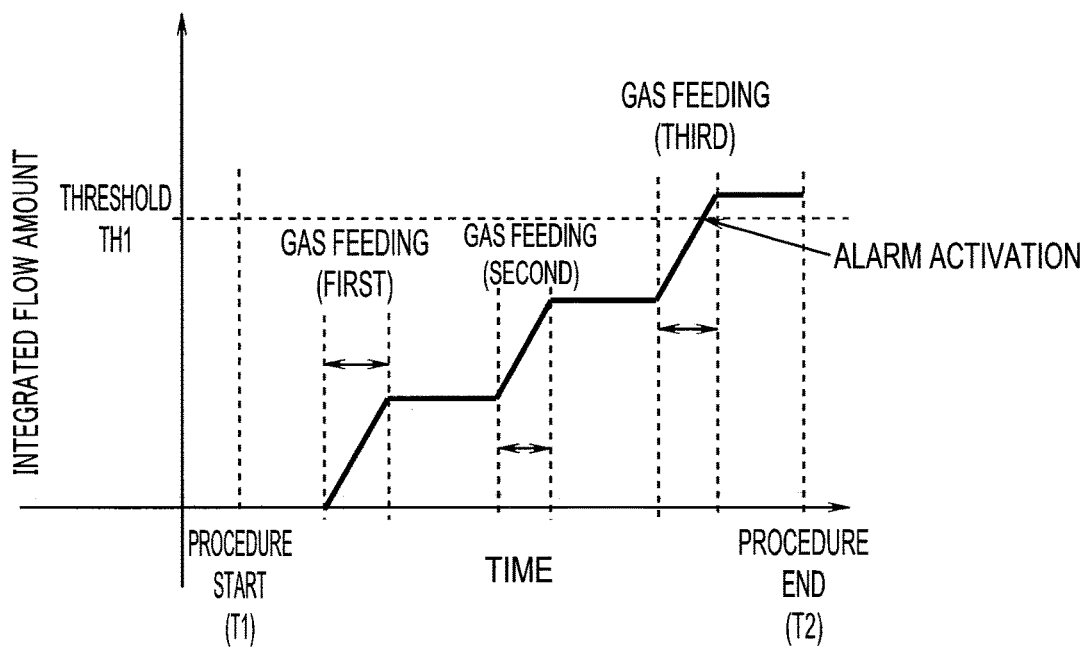
FIG. 3 is a diagram for describing an alarm activation timing based on the integrated flow amount.

FIG. 3 is a diagram for describing an alarm activation timing based on the integrated flow amount. As an example, FIG. 3 shows a case where three gas feedings are performed during one procedure. The integrated gas feeding amount does not reach the previously set threshold TH1 during the first and second gas feedings, but reaches the threshold TH1 during the third gas feeding. In other words, during the third gas feeding, at the time when the integrated gas feeding amount reaches the previously set threshold TH1, the control circuit 16 activates the alarm by causing the notification unit 20 to act, and thereby, the user can recognize the integrated gas feeding amount.

For example, the threshold TH1 can be set as follows. Here, a case where the gas feeding flow rate is relatively high and the excessive gas feeding easily occurs is discussed. For example, in the case of 1.5 L/min, among ratios of gas feeding time periods in examinations, the most frequent gas feeding time period is 11 seconds to 20 seconds. Assuming that the time period of one gas feeding is 15 seconds, the gas feeding amount for one gas feeding is $1.5\times(15/60)=0.4$ L. Assuming that the number of gas feedings for one procedure is 15, the gas feeding amount is $0.4\times15=6$ L. In addition, a gas feeding, the time period of which is less than 5 seconds, is frequently performed in medical treatments, and therefore, for example, assuming that a 2-second gas feeding is performed 30 times, the gas feeding amount is $1.5\times(2/60)\times30=1.5$ L. Accordingly, the threshold TH1 for one procedure can be set to $6+1.5=7.5$ L. Generally, it is preferable that the threshold TH1 should be set to a predetermined flow amount between 5 L and 30 L, which is just one example because the gas feeding flow rate and the gas feeding time period vary depending on the procedure, the gas feeding site and the operator.

In the case where the site for the gas feeding is a site where there is little space for letting the gas out and the gas easily accumulates, the management based on the integrated gas feeding amount during the whole procedure is effective, as shown in FIG. 3.

Second Embodiment

The above-described gas feeding apparatus 1 in the first embodiment monitors the integrated gas feeding amount in a predetermined time period, for detecting the alarm activation timing for the excessive gas feeding. In contrast, the embodiment is different in that an elapsed time period from the gas feeding start is monitored. The gas feeding apparatus in the embodiment is the same as the gas feeding apparatus 1 in the first embodiment shown in FIG. 1, and therefore, the description is omitted.

Figure 4:
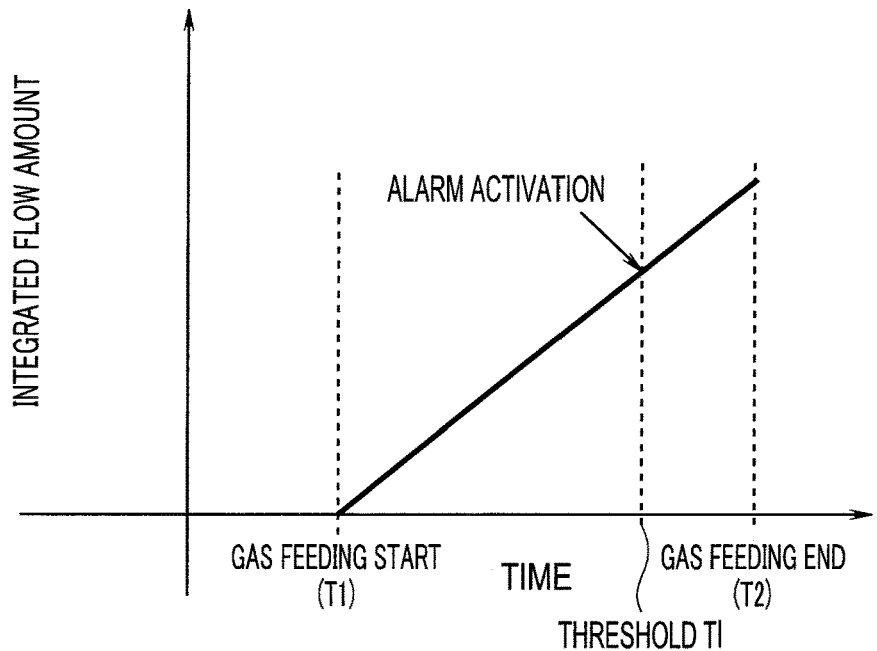
FIG. 4 is a diagram for describing an alarm activation timing based on an elapsed time period from a gas feeding start.

An action of the control circuit 16 in the embodiment will be described below with use of FIG. 4. FIG. 4 is a diagram for describing an alarm activation timing based on the elapsed time period from the gas feeding start.

The control circuit 16 counts a gas feeding elapsed time period in a designated period from a time point T1 to a time period T2. For example, the time point T1 is a timing when the gas feeding button 41 of the endoscope 30 is pressed down and the gas starts to be fed from the distal end portion 31 of the insertion unit 35 into the lumen. While the pressed-down state of the gas feeding button 41 is continued, the gas feeding is continued. As the time point T2, it is possible to adopt a timing when the pressed-down state of the gas feeding button 41 of the endoscope 30 is released and the gas stops being fed from the distal end portion 31 of the insertion unit 35 into the lumen.

The control circuit 16 activates the alarm to the user by causing the notification unit 20 to act, at the time when the gas feeding elapsed time period reaches a previously set threshold in the period from the time point T1 to the time point T2. As the action of the notification unit 20 at the time of the alarm activation, for example, the notification unit 20 causes the user to visually perceive the alarm by lighting a lamp or causes the user to aurally perceive the alarm by activating a buzzer or a warning message.

In this way, in the embodiment, the control circuit 16 counts the gas feeding elapsed time period in the decided period from the time point T1 to the time point T2. At the time when the gas feeding elapsed time period reaches the previously set threshold T1, the control circuit 16 activates the alarm by causing the notification unit 20 to act, and thereby, the user can recognize the integrated gas feeding time period. Accordingly, even when the user is concentrating on the observation or treatment of an organ in the lumen and loses awareness about the gas feeding, it is possible to raise awareness about the gas feeding at a necessary time, and to prevent the excessive gas feeding into the lumen.

Note that the embodiment may also count a total integrated gas feeding time period during one procedure instead of counting the gas feeding elapsed time period for one procedure and may give the alarm when the total integrated gas feeding time period exceeds the threshold.

Third Embodiment

The above-described gas feeding apparatus 1 in the first embodiment activates the alarm for the excessive gas feeding when the integrated gas feeding amount in the predetermined time period exceeds the predetermined threshold TH1. In contrast, the embodiment is different in that two levels of thresholds TH1, TH2 are provided and the warning content and method are changed in a stepwise manner. The gas feeding apparatus in the embodiment is the same as the gas feeding apparatus 1 in the first embodiment shown in FIG. 1, and therefore, the description is omitted.

Figure 5:
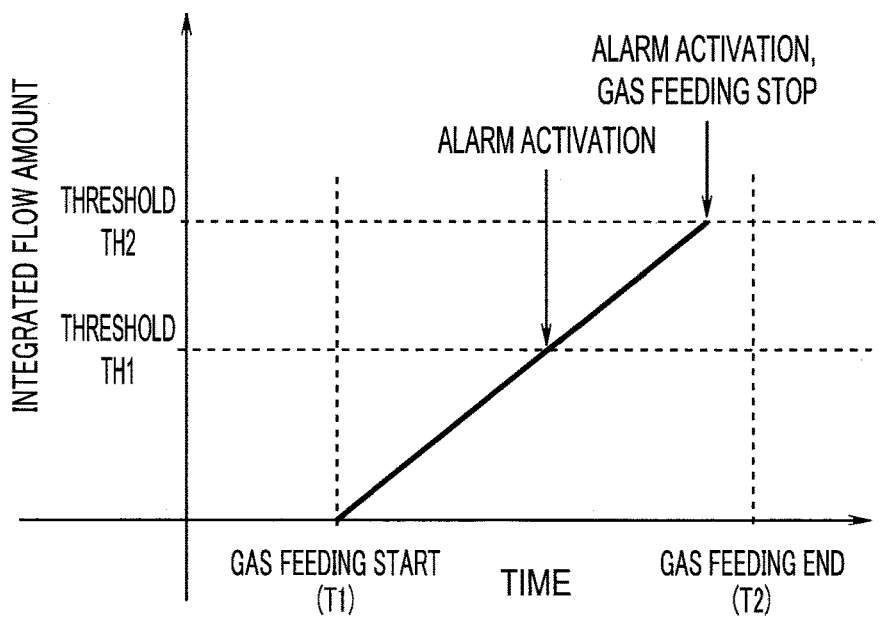
FIG. 5 is a diagram for describing an alarm activation timing and a gas feeding stop timing based on the integrated flow amount.

An action of the control circuit 16 in the embodiment will be described below with use of FIG. 5. FIG. 5 is a diagram for describing an alarm activation timing and a gas feeding stop timing based on the integrated flow amount. The control circuit 16 time-sequentially integrates the gas feeding amount in a designated period from a time point T1 to a time point T2 (for example, in a period from the gas feeding start to the gas feeding end), based on the flow rate measurement value inputted from the flow rate sensor 14. In the control circuit 16, the two levels of thresholds TH1, TH2 (threshold TH1<threshold TH2) are previously set. At the time when the integrated gas feeding amount reaches the previously set threshold TH1 in the period from the time point T1 to the time point T2, the control circuit 16 activates the alarm to the user by causing the notification unit 20 to act. As the action of the notification unit 20 at the time of the alarm activation, for example, the notification unit 20 causes the user to visually perceive the alarm by lighting a lamp or causes the user to aurally perceive the alarm by activating a buzzer or a warning message. At the time when the integrated gas feeding amount reaches the previously set threshold TH2 after a further time elapse, the control circuit 16 activates the alarm again and automatically stops the gas feeding.

By providing two levels of thresholds in this way, even when the user misses the first alarm and continues the gas feeding, it is possible to automatically stop the gas feeding before transition to a dangerous state. Accordingly, even when the user is concentrating on the observation or treatment of an organ in the lumen and loses awareness about the gas feeding, it is possible to surely prevent the excessive gas feeding into the lumen.

Fourth Embodiment

The above-described gas feeding apparatus 1 in the first embodiment activates the alarm for the excessive gas feeding when the integrated gas feeding amount in the predetermined time period exceeds the predetermined threshold TH1. In contrast, the embodiment is different in that the gas feeding flow rate is gradually reduced whenever a predetermined time period elapses after the integrated gas feeding amount exceeds the threshold TH1. The gas feeding apparatus in the embodiment is the same as the gas feeding apparatus 1 in the first embodiment shown in FIG. 1, and therefore, the description is omitted.

Figure 6:
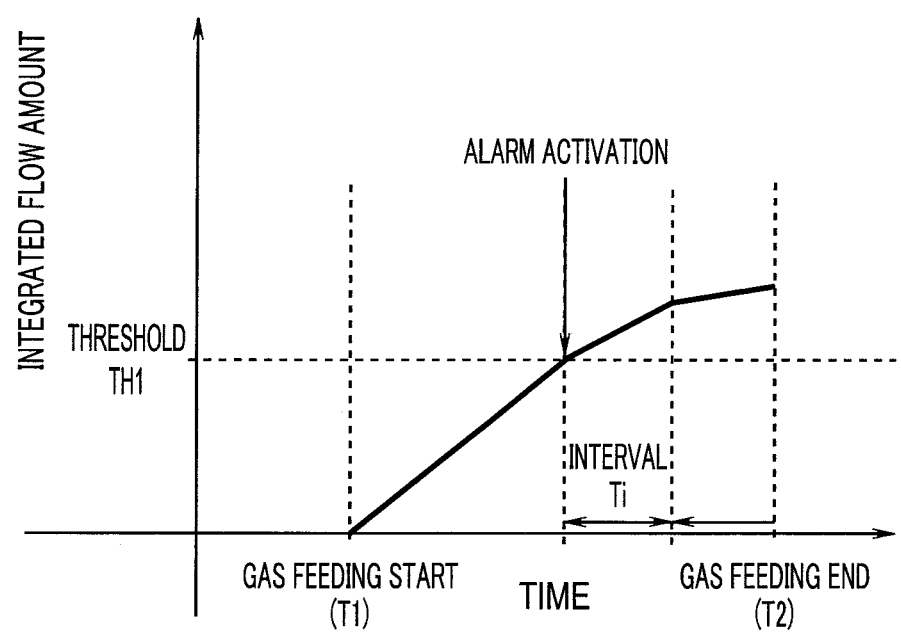
FIG. 6 is a diagram for describing a temporal change in a gas feeding flow rate control based on the integrated flow amount.

An action of the control circuit 16 in the embodiment will be described below with use of FIG. 6. FIG. 6 is a diagram for describing a temporal change in a gas feeding flow rate control based on the integrated flow amount. The control circuit 16 time-sequentially integrates the gas feeding amount in a designated period from a time point T1 to a time point T2 (for example, in a period from the gas feeding start to the gas feeding end).

At the time when the integrated gas feeding amount reaches the set threshold TH1, the control circuit 16 activates the alarm to the user by causing the notification unit 20 to act. As the action of the notification unit 20 at the time of the alarm activation, for example, the notification unit 20 causes the user to visually perceive the alarm by lighting a lamp or causes the user to aurally perceive the alarm by activating a buzzer or a warning message. From the time when the integrated gas feeding amount reaches the threshold TH1, the control circuit 16 controls the flow rate control valve 13 to reduce the flow rate of the gas by a predetermined rate (for example, reduces the flow rate to half the selling flow rate). When a preset time period Ti elapses from the time when the integrated gas feeding amount reaches the threshold TH1, the control circuit 16 controls the flow rate control valve 13 to reduce the flow rate of the gas by the predetermined rate.

For example, in the case where the setting flow rate is 2 L/min and the flow rate reduction rate is 50%, the setting flow rate before the predetermined time period Ti elapses from the time when the integrated gas feeding amount reaches the threshold TH1 is controlled to 1 L/min. Further, the setting flow rate after the predetermined time period Ti elapses from the time when the integrated gas feeding amount reaches the threshold TH1 is controlled to 0.5 L/min.

By reducing the flow rate of the gas whenever the predetermined time period elapses after the integrated gas feeding amount reaches the threshold TH1 in this way, it is possible to prevent the excessive gas feeding into the lumen without completely stopping the gas feeding into the lumen.

Fifth Embodiment

Figure 7:
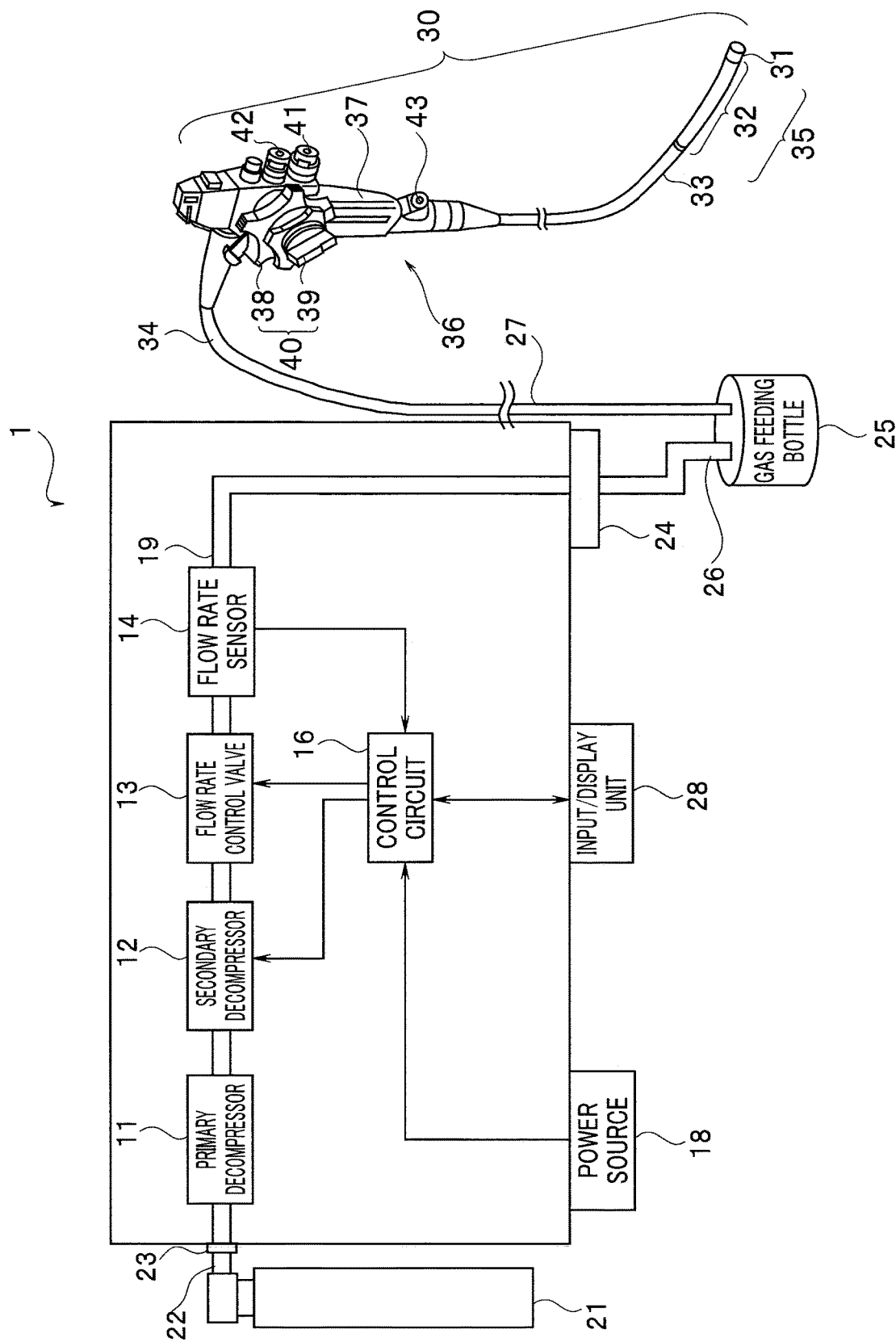
FIG. 7 is a diagram for describing an example of a gas feeding apparatus 1 according to a fifth embodiment.

A gas feeding apparatus in the embodiment displays the content of the alarm on a screen, in addition to the above-described gas feeding apparatuses in the first to fourth embodiments. FIG. 7 is a diagram for describing an example of a gas feeding apparatus 1 according to the fifth embodiment. The gas feeding apparatus in the embodiment is different in that the component elements described so as to be separated as the operation switch 15, the setting input unit 17 and the notification unit 20 in the gas feeding apparatus 1 in the first embodiment shown in FIG. 1 correspond to an input/display unit 28 configured by a touch panel, for example. The other component elements are the same, and therefore, the description is omitted.

Figure 8:
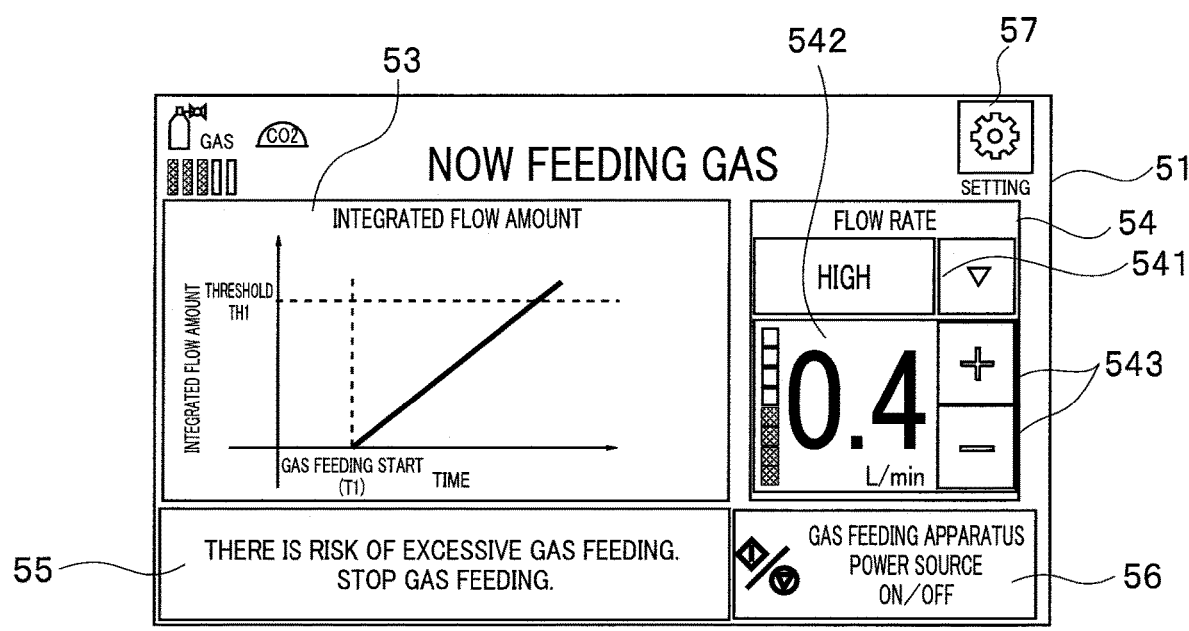
FIG. 8 is a diagram for describing an example of an alarm display screen.

FIG. 8 is a diagram for describing an example of an alarm display screen. FIG. 8 shows an example of the display content of the input/display unit 28 in the case where the integrated flow amount or the elapsed time period from the gas feeding start exceeds the predetermined threshold and where the alarm is given. As shown in FIG. 8, respective display regions of an integrated flow amount display region 53, a flow rate display region 54 and a message display region 55 are provided on an alarm display screen 51 of the input/display unit 28.

On the integrated flow amount display region 53, the value resulting from integrating, with the control circuit 16, the flow amount of the gas measured by the flow rate sensor 14 is displayed as a graph, for example. It is preferable that a level of the threshold TH1 should be shown on the graph and should be displayed such that it is easy to visually perceive how much the current integrated flow amount is exceeding the threshold TH1.

On the flow rate display region 54, a combo box 541 for setting a flow rate mode, a flow rate display portion 542 and a flow rate setting button 543 are disposed. The flow rate mode is a mode that is previously set depending on the lumen as a gas feeding target, an operative method and the like, and for example, three modes of High, Middle and Low are prepared. Flow rate setting values corresponding to the respective modes are registered in an unillustrated memory, and when the flow rate mode is altered by an operation of the combo box, a flow rate setting value registered in association with a flow rate mode after the alteration is read from the memory, and is displayed on the flow rate display portion 542.

The flow rate setting button 543 is a button that is used for designating a numerical value of the flow rate setting value. When "+" in the flow rate setting button 543 is pressed down, the flow rate setting value increases, and when "−" is pressed down, the flow rate setting value decreases. In other words, the scale of a level meter in the flow rate display portion 542 is altered depending on the flow rate setting value that is set using the combo box 541 or the flow rate setting button 543.

On the alarm display screen 51, the message display region 55 where the content of the alarm can be displayed as characters is further provided.

On the alarm display screen 51, an action button 56 for controlling the start/stop of the action of the gas feeding apparatus and a setting button 57 for calling a setting screen on which setting for each site of the apparatus is performed are further provided. Furthermore, display portions, setting buttons and others corresponding to functions of the gas feeding apparatus 1 are appropriately disposed.

By not only giving the alarm hut also displaying the content of the alarm on the screen in this way, it is easy for the user to visually recognize the content of the alarm, and it is possible to quickly take a countermeasure for preventing the excessive gas feeding.

Note that the screen shown in FIG. 8 is an example, and the alarm screen may be configured by only the message display region 55 without the integrated flow amount display region 53, or the content of the alarm may be displayed in another display form. Further, the content of the alarm may be displayed not only on the input/display unit 28 of the gas feeding apparatus 1 but also on another display apparatus such as a main monitor in an operating room or a monitor for intensively managing other apparatuses and others.

Although some embodiments of the present invention have been described, the embodiments have been shown as examples, and it is not intended to limit the scope of the invention. The novel embodiments can be carried out in a variety of other modes, and various omissions, replacements and alterations can be performed without departing from the spirit of the invention. The embodiments and the modifications are included in the scope and spirit of the invention, and are included in a scope equivalent to the invention described in the claims.

What is claimed is:

1. A gas feeding apparatus for use with an endoscope, the gas feeding apparatus comprising
  a sensor configured to measure a flow rate of a gas and output a measurement result; and
  a control circuit configured to:
    set a first threshold for one of an integrated amount of the gas or a gas feeding time period of the gas;
    set a second threshold for one of the integrated amount of the gas or the gas feeding time period of the gas, the second threshold being larger than the first threshold;
    time-sequentially calculate the integrated amount of the gas or the gas feeding time period of the gas in a period from a first timing to a second timing based on the measurement result, the first timing being a timing when the gas starts to be fed, the second timing being different from the first timing;
    control a notification device to activate an alarm, when a calculation result of one of the integrated amount of the gas or the gas feeding time period of the gas reaches the first threshold in the period from the first timing to the second timing; and
    stop the gas feeding when the calculation result reaches the second threshold.

2. The gas feeding apparatus according to claim 1, wherein the control circuit is configured to adopt timing when the measurement result starts to rise from a value close to zero, as the first timing.

3. The gas feeding apparatus according to claim 2, wherein the control circuit is configured to adopt a timing when the measurement result starts to decrease in a state where the measurement result is kept at a predetermined value, as the second timing.

4. The gas feeding apparatus according to claim 1, wherein the control circuit is configured to adopt a procedure start as the first timing, and adopt a procedure end as the second timing.

5. The gas feeding apparatus according to claim 1, wherein the control circuit is configured to reduce the flow rate of the gas, when the calculation result reaches the first threshold.

6. The gas feeding apparatus according to claim 5, wherein the control circuit is configured to set a predetermined time interval, and reduce the flow rate of the gas, whenever the predetermined time interval elapses after the calculation result reaches the first threshold.

7. The gas feeding apparatus according to claim 1, wherein the control circuit is configured to control the notification device to activate the alarm again, when the calculation result reaches the second threshold in the period from the first timing to the second timing.

8. The gas feeding apparatus according to claim 1, further comprising a gas feeding conduit communicating with a conduit disposed in the endoscope.

9. A method for feeding gas with an endoscope, the method comprising:
   measuring, by a sensor, a flow rate of a gas and outputting a measurement result;
   setting, by a control circuit, a first threshold for one of an integrated amount of the gas or a gas feeding period of the gas;
   setting, by the control circuit, a second threshold for one of the integrated amount of the gas or the gas feeding time period of the gas, the second threshold being larger than the first threshold;
   time-sequentially calculating, by the control circuit, the integrated amount of the gas or the gas feeding time period of the gas in a period from a first timing to a second timing based on the measurement result, the first timing being a timing when the gas starts to be fed, the second timing being different from the first timing;
   controlling, by the control circuit, a notification device to activate an alarm, when a calculation result of one of the integrated amount of the gas or the gas feeding time period of the gas reaches the first threshold in the period from the first timing to the second timing; and
   stopping, by the control circuit, the gas feeding when the calculation result reaches the second threshold.

10. A gas feeding system comprising:
    the endoscope; and
    the gas feeding apparatus according to claim 1.

11. A gas feeding apparatus for use with an endoscope, the gas feeding apparatus comprising:
    a sensor configured to measure a flow rate of a gas and output a measurement result; and
    a control circuit configured to:
      set a first threshold for one of an integrated amount of the gas or a gas feeding time period of the gas;
      set a predetermined time interval;
      time-sequentially calculate the integrated amount of the gas or the gas feeding time period of the gas in a period from a first timing to a second timing based on the measurement result, the first timing being a timing when the gas starts to be fed, and the second timing being different from the first timing;
      control a notification device to activate an alarm when a calculation result of the one of the integrated amount of the gas or the gas feeding time period of the gas reaches the first threshold in the period from the first timing to the second timing; and
      reduce the flow rate of the gas whenever the predetermined time interval elapses after the calculation result reaches the first threshold.

12. The gas feeding apparatus according to claim 11, wherein the control circuit is configured to adopt a timing when the measurement result starts to rise from a value close to zero, as the first timing.

13. The gas feeding apparatus according to claim 12, wherein the control circuit is configured to adopt a timing when the measurement result starts to decrease in a state where the measurement result is kept at a predetermined value, as the second timing.

14. The gas feeding apparatus according to claim 11, wherein the control circuit is configured to adopt a procedure start as the first timing, and adopt a procedure end as the second timing.

15. The gas feeding apparatus according to claim 11, further comprising a gas feeding conduit communicating with a conduit disposed in the endoscope.

16. A gas feeding system comprising the endoscope and the gas feeding apparatus according to claim 11.

* * * * *